United States Patent [19]

Ishikawa

[11] Patent Number: 4,575,181

[45] Date of Patent: Mar. 11, 1986

[54] OPTICAL FIBER ASSEMBLY WITH CLADDING LIGHT SCATTERING MEANS

[75] Inventor: Ken Ishikawa, Yokohama, Japan

[73] Assignee: Tokyo Shibaura Denki Kabushiki Kaisha, Kawasaki, Japan

[21] Appl. No.: 488,704

[22] Filed: Apr. 26, 1983

[51] Int. Cl.$^4$ .............................................. G02B 7/26
[52] U.S. Cl. ............................... 350/96.20; 350/96.33
[58] Field of Search ............... 350/96.10, 96.20, 96.21, 350/96.22, 96.29, 96.30, 96.33; 250/227; 357/17, 18, 19, 30, 74, 75

[56] References Cited

U.S. PATENT DOCUMENTS

| | | | |
|---|---|---|---|
| 3,386,043 | 5/1968 | Marcatili | 330/4.3 |
| 3,995,934 | 12/1976 | Nath | 350/96.10 |
| 4,270,134 | 5/1981 | Takeda et al. | 357/19 |
| 4,316,204 | 2/1982 | Inagaki et al. | 350/96.20 |
| 4,421,382 | 12/1983 | Doi et al. | 350/96.20 |
| 4,422,719 | 12/1983 | Orcutt | 350/96.10 |

FOREIGN PATENT DOCUMENTS

| | | | |
|---|---|---|---|
| 126208 | 9/1980 | Japan | 350/96.15 |
| 78002 | 5/1982 | Japan | 350/96.10 |

OTHER PUBLICATIONS

Wielar, Conference: Proc. of the Soc. of Photo-Optical Instrumentation Engineers, Seminar on Fibre Optics Come of Age, vol. 31, San Mateo, Calif., U.S.A., 16–17 Oct. 1972, "Plastic Optical Fibers," pp. 3–12.

Primary Examiner—William L. Sikes
Assistant Examiner—Frank González
Attorney, Agent, or Firm—Cushman, Darby and Cushman

[57] ABSTRACT

In an optical fiber assembly, an optical fiber having a core and a cladding is covered with a protecting film. The film is removed in a predetermined region extending from the end face of the optical fiber along the optical fiber, and the cladding is exposed. The surface of the exposed cladding is formed with a rough surface, and a laser beam which is transmitted to the cladding is scattered externally from the rough surface. The optical fiber is mounted on the hollow holder, and the rough surface of the cladding is disposed in the holder. The beam component scattered externally from the rough surface is absorbed by the light absorbing layer on the inner surface of the holder.

9 Claims, 4 Drawing Figures

OPTICAL FIBER ASSEMBLY WITH CLADDING LIGHT SCATTERING MEANS

BACKGROUND OF THE INVENTION

The present invention relates to an optical fiber assembly and, more particularly, to an optical fiber assembly for transmitting a laser beam of high energy.

An optical fiber is used to transmit a laser beam in an optical communication system, an optical measurement system, a medical application system such as a laser knife in medical treatment and a machining system in industrial processes such as a marking, machining, cutting and engraving system. This optical fiber includes a core and a cladding for covering the core. The outer periphery of this cladding is covered with a protecting film, namely a primary coat of silicon and a jacket of polyamide.

In general, when a laser beam is transmitted through such an optical fiber, the laser beam is converged into a core in the range of the accepting angle of the optical fiber which is defined by the numerical aperture (NA) of the fiber and is transmitted through the core from the incident end to the emitting end. However, the directivity and the beam divergence of the laser beam is varied when the laser output power is changed, thereby causing the beam to fluctuate. So that, when the beam is focussed on the end face of the optical fiber, the beam spot is not only formed on the core section on the end face of the optical fiber but is also formed on the cladding section due to the fluctuation of the beam. In other words, the main component of the beam is transmitted through the core, but the other component of the beam incident on the cladding is propagated through the cladding.

When a higher energy than 20 or 30 watts; e.g., several kilowatts is transmitted by the optical fiber as in a carbon dioxide gas laser or a YAG laser energy transmission, the protecting film on the outer periphery of the cladding at the beam incident face of the optical fiber is often damaged by the temperature rise caused by laser beam leakage from the cladding to the film or by the beam being directly incident on the film. In these cases, the optical fiber may also be dropped from the member for holding the fiber because of film softening caused by this temperature rise. Similar problems occurs at the light emitting end when a portion of the laser beam is reflected from the reflecting material located near the emitting end to the above-mentioned emitting end. In this case, the same type of problem exists at the emitting end as discussed above with respect to the light incident end.

Heretofore, in order to prevent the protecting film of the optical fiber from being damaged, the beam incident on the optical fiber has been limited in power to about 20–30 W. An optical fiber in which the protecting film is not readily thermally damaged is strongly desired for a high energy laser beam transmission.

SUMMARY OF THE INVENTION

It is an object of the present invention to provide an optical fiber assembly which is capable of transmitting a laser beam having high energy without damaging a protecting film of the assembly.

According to one aspect of the present invention, there is provided an optical fiber assembly comprising: an optical fiber having a core, a cladding for covering the core and an end face on which a laser beam is incident for transmitting a laser beam, a protecting film for covering the optical fiber, and means formed on the outer surface region of the cladding covered with no protecting film and extending from the end face along the optical fiber, for directing the laser beam component introduced into the cladding out of the cladding.

DETAILED DESCRIPTION OF THE PREFERRED EMBODIMENTS

Figure 1:
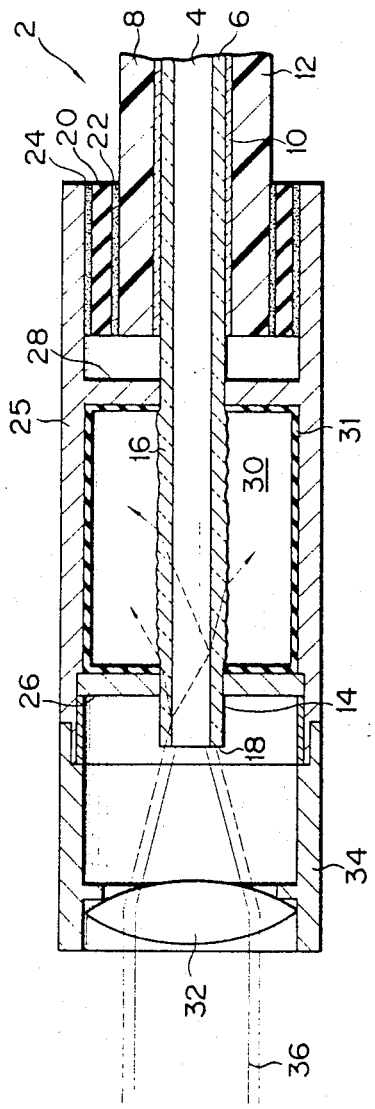
FIG. 1 is a sectional view showing an optical fiber assembly according to an embodiment of the present invention.

FIG. 1 shows the structure of the end part of an optical fiber assembly according to an embodiment of the present invention. An optical fiber 2 has, as is known, a core 4 and a cladding 6 which covers the core 4. The cladding 6 is covered with a protecting film 8. The film 8 is formed, for example, of a primary coat 10 of silicon resin coated on the surface of the cladding 6 and a jacket 12 of polyamide coated on the outer surface of the primary coat.

In this embodiment, the film 8 of the optical fiber is removed in a predetermined length such as, for example, 20 cm from the end of the optical fiber 2, and the surface of the cladding 6 is exposed at the section 14. In this section 14, the surface 16 of the cladding 6 is made rough. The length of the rough surface 16 is formed from the end face 18 of the fiber 2 along the optical axis of the fiber 2 for about 20 cm, preferably 5 cm. Surface 16 can be roughened, for example, by polishing the surface of the cladding with diamond powder or treating the surface with a chemical etchant.

A heat insulating material 20 such as asbestos is bonded with a refractory adhesive 22 to the outer periphery of the end part of the protecting film 8 of the fiber 2 and is inserted into a cylindrical holder 25 which is formed of a thermally conductive metal. It is then fixedly secured similarly with a refractory adhesive 24 into the holder 25, and the fiber 2 is fixed to the holder 25. Positioning rings 26 and 28 are provided in the holder 25, the exposed section 14 of the cladding 6 is inserted into holes formed between the rings 26 and 28 along the axis of the holder 25, and is supported by the rings 26 and 28. A cavity 30 which absorbs the light energy is defined by the inner surfaces of a pair of the rings 26 and 28 and the holder 25, and the rough surface 16 of the cladding 6 is disposed in the cavity 30. A layer 31 which absorbs the light is adhered to the inner surfaces of the rings 26 and 28 and the holder 22 for defining the cavity 30.

A cylindrical lens holder 34 for holding a convergent lens 32 is engaged with the one end opening of the holder 25. The distance between the lens 32 and the end face 18 of the fiber 2 is defined so that the beam passed through the lens 32 forms a beam waist or a beam spot slightly larger than the beam waist on the end face 18.

The lens 32 and the fiber 2 are arranged so that the beam passed through the lens 32 forms a beam waist or a beam spot on the core of the end face.

In the optical fiber structure described above, a laser beam having high power can be transmitted as below.

A light transmission in the structure described above will be described. A laser beam 36 is passed through the lens 32 to form a beam spot on the end surface of the core 4. The size of the spot varies depending upon the beam divergence and the directivity of the beam which is emitted from the laser unit. The beam divergence and the directivity of the beam not only sequentially vary from the time the oscillation starts but also vary in accordance with the output level of oscillation. Accordingly, part of the beam is also incident on the part of the cladding 6 designated by broken lines in FIG. 1. The part of the beam component incident on the cladding 6 is reflected on the outer surface of the core 4 of the boundary between the core 4 and the cladding 16 in the exposed section 14 of the cladding 16, and is thus directed toward the outer surface of the cladding 16. This beam component is not reflected again to the side of the core 4 on the rough surface 16, but is scattered externally. The other part of the beam component incident on the cladding 6 is incident on the core 4 from the cladding 6 and is passed through the core 4 to the cladding 6. Thus, the beam component is not reflected into the core but is dissipated outside of the fiber from the rough surface 16. Accordingly, the beam which is thus passed through the section 14 of the cladding 16 is only the component enclosed in the core 4. Therefore, even if the beam is propagated to a predetermined section of the protecting film 8, the beam component incident on the cladding 16 from the end surface of the section 14 is removed as described above. Consequently, the drawback of abnormal increases in temperature of the protecting film damaging the film is eliminated. On the other hand, the beam component which is emitted externally from the rough surface 16 is absorbed by the light absorbing layer 31, and the heat is radiated externally through the holder 25. In this case, even if the holder 25 and the layer 31 are not provided, the light which is emitted externally has lost its directivity, and does not have a detrimental influence on a human body.

Since only the beam component of the beam incident on the fiber 2 which is enclosed in the core 4 is propagated to the part of the optical fiber provided with the protecting film 8, the optical fiber itself is prevented from being damaged, thereby making possible the use of laser beams of greater power (approx. 300 W). Further, since the beam emitted from the optical fiber includes only the beam which is propagated in the core 4, a small spot can be formed to thereby machine the workpiece more precisely. When the laser beam is projected from the optical fiber, the beam emitting end of the fiber is damaged by the beam reflected from the workpiece, and it is accordingly necessary to construct the beam emitting end as described above.

Figure 2:
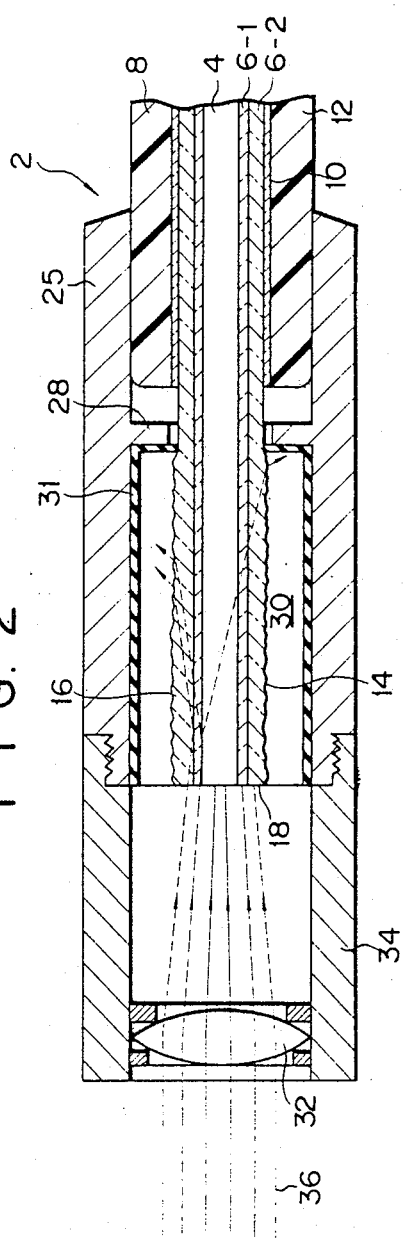
FIG. 2 is a sectional view showing an optical fiber assembly according to another embodiment of the present invention.

The FIG. 1 arrangement is directed to an embodiment of the present invention in which a step type optical fiber having a core 4 and a cladding 6 is used. However, the present invention may also be applied to an optical fiber of the multicladding type as shown in FIG. 2. More particularly, a core 4 having a refractive index $n_1$ is covered with a first cladding 6-1 having a refractive index $n_2$ lower than the index $n_1$ and the cladding 6-1 is further covered with a second cladding 6-2 having a refractive index $n_3$ equal to or lower than the index $n_1$ and higher than the index $n_2$. In this fiber 2, the protective film 8 is similarly removed and is formed with a rough surface 16 at the section 14 of the cladding 6-2. The other parts and positions are similar to the structure shown in FIG. 1, and are designated with the same reference numerals and will be omitted for the description. However, in the optical fiber device shown in FIG. 2, the insulating material 20 is not provided on the outer periphery of the protecting film 8, but it is noted that the fiber 2 is mounted directly on the holder 25.

In the optical fiber assembly described above, even when a laser beam is emitted to the end faces of the core 4 and the cladding 6-1, 6-2, only the component which is incident on the core 4 is propagated. In other words, a beam component which is incident within the acceptance angle of the fiber 2 on the core 4 is propagated in the core 4, but the beam which is incident on the first cladding 6-1 is gradually weakened because the beam component is entered into the core 4 or into the second cladding 6-2. The beam component which is entered into the second cladding 6-2 is reflected from the boundary between the first and second claddings 6-1 and 6-2, is thus directed to the outer surface of the second cladding 6-2 since the outer surface of the second cladding 6-2 is formed on the optically rough surface 16 as described above, the beam components are not accordingly completely reflected from the outer surface the second cladding 6-2, are scattered outside of the optical fiber and absorbed by the beam absorbing surface 31. Further, it is impossible to transmit the beam from the end face through the second cladding 6-2 over a long distance, since the beam incident on the end face is converged, light rays which are incident at predetermined angles with respect to the optical axis of the fiber and all light rays are directed to the rough surface 16 of the second cladding 6-2.

Figure 3:
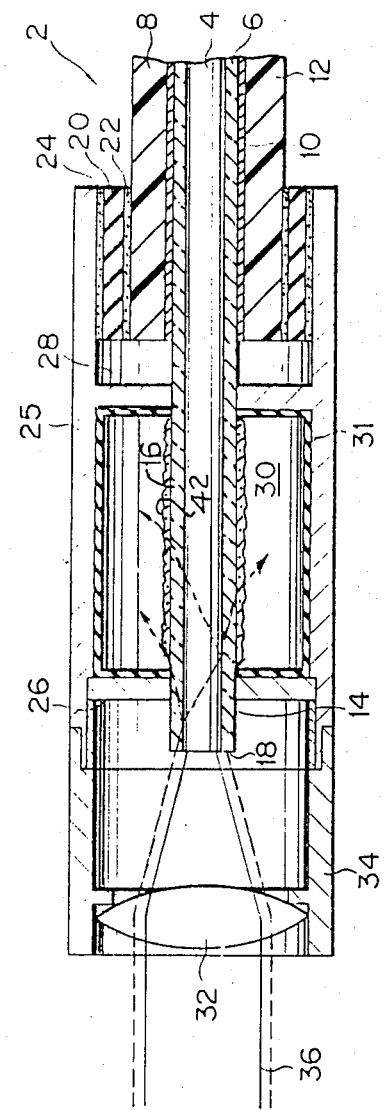
FIG. 3 is a sectional view showing an optical fiber assembly according to one modified embodiment of the present invention.
Figure 4:
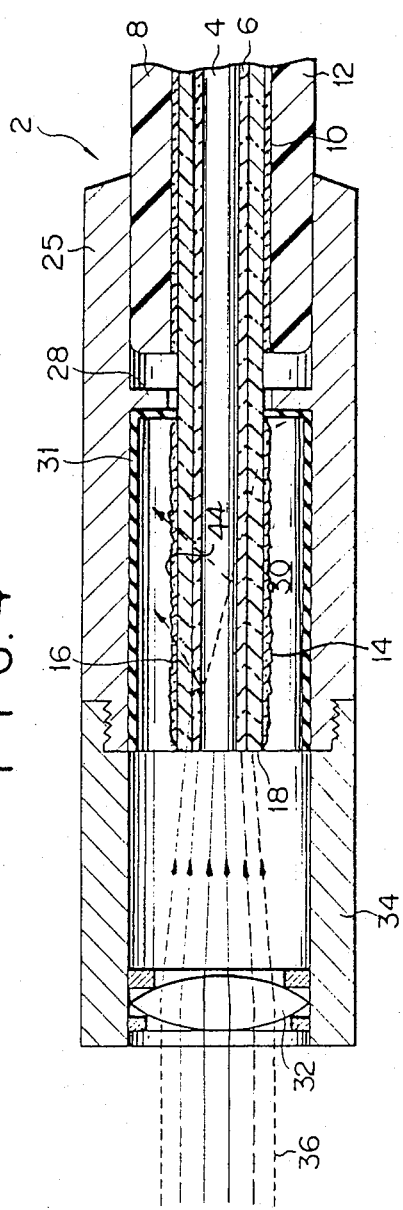
FIG. 4 is a sectional view showing an optical fiber assembly according to another modified embodiment of the present invention.

In all the embodiments described above, the rough surface 16 may alternatively be formed by being coated with a material 42 having a similar refractive index to the cladding as shown in FIG. 3 or it may be bonded with particles 44 having a similar refractive index to the cladding. Either of these alternatives would substitute for polishing with diamond powder, as shown in FIG. 4.

According to the present invention as described above, an optical fiber assembly which can transmit a laser beam having high energy without damaging the protecting film is provided.

What is claimed is:

1. An optical head assembly for coupling a laser beam to an optical fiber comprising:

an optical fiber having a core and a cladding covering the core and an end face for receiving said laser beam;

a protection film covering a portion of said cladding;

means, formed on a predetermined outer surface region of said cladding on which there is no protection film and which extends along the optical fiber, for scattering a component of the laser beam introduced into the cladding out of the cladding;

a heat conductive case encapsulating the scattering means and having an inner surface separated from the scattering means; and absorbing means formed on the inner surface of the heat conductive case for absorbing the laser beam component scattered from said scattering means.

2. An optical head assembly according to claim 1, wherein said scattering means is a rough surface formed on the outer surface region of the cladding.

3. An optical head assembly according to claim 2, wherein the rough surface comprises a roughened surface of the cladding.

4. An optical head assembly according to claim 2, wherein the rough surface comprises a coating on the surface of the cladding of a material having a refractive index substantially equal to the cladding.

5. An optical head assembly according to claim 2, wherein the rough surface comprises particles bonded to the surface of the cladding which particles have a refractive index substantially equal to cladding.

6. An optical head assembly according to claim 2, wherein the rough surface treated by a chemical etchant.

7. An optical head assembly according to claim 1, wherein said heat conductive case is a hollow holder formed of thermally conductive material.

8. An optical head assembly according to claim 7, further comprising a non-thermally conductive member interposed between the optical fiber and the hollow holder.

9. An optical fiber assembly according to claim 7, wherein the absorbing layer is formed on the inner surface of the hollow holder.

* * * * *